US006945094B2

(12) United States Patent
Eggen et al.

(10) Patent No.: US 6,945,094 B2
(45) Date of Patent: Sep. 20, 2005

(54) VISCOSITY MEASUREMENT (75) Inventors: Svein Eggen, Langangen (NO); Kim Esbensen, Larvik (NO); Mats Halstensen, Hamur (NO)

(73) Assignee: Borealis Technology Oy, Porvoo (FI)

(*) Notice: Subject to any disclaimer, the term of this patent is extended or adjusted under 35 U.S.C. 154(b) by 0 days.

(21) Appl. No.: 10/451,226

(22) PCT Filed: Dec. 21, 2001

(86) PCT No.: PCT/GB01/05771

§ 371 (c)(1),
(2), (4) Date: Oct. 8, 2003

(87) PCT Pub. No.: WO02/052243

PCT Pub. Date: Jul. 4, 2002

(65) Prior Publication Data

US 2004/0060345 A1 Apr. 1, 2004

(30) Foreign Application Priority Data

Dec. 22, 2000 (GB) .............................. 0031564

(51) Int. Cl.$^7$ .................. G01N 11/00; G01N 17/00; G01N 29/02
(52) U.S. Cl. .................. 73/54.41; 73/54.01; 73/587
(58) Field of Search .................. 73/54.01, 54.24, 73/54.41, 587

(56) References Cited

U.S. PATENT DOCUMENTS 3,816,773 A 6/1974 Baldwin et al.
3,906,780 A 9/1975 Baldwin (Continued)

FOREIGN PATENT DOCUMENTS

| CN | 1233752 | 3/1999 |
| EP | 0 390 835 B1 | 6/1989 |
| EP | 0 317 322 B1 | 1/1993 |
| EP | 0933632 | 8/1999 |
| GB | 1 346 095 A | 6/1974 |
| GB | 2 038 851 A | 7/1980 |
| WO | WO 97/38292 | 10/1997 |
| WO | 00/33051 A | 6/2000 |

OTHER PUBLICATIONS

Kim et al, "A Study on treeing Breakdown and Fractal Characteristics according to Method of Acoustic Emission Detection in High Polymer", Proceedings of the 5$^{th}$ International Conference on Properties and Applications of Dielectric Materials, May 25–30, 1997, Seoul, Korea, pp. 434–438; XP010242484.

Bettinger, "Microprocessor Based System for the Detection and Characterization of Acoustic Emissions for Materials Testing", Bradley Dept. of Electrical Engineering, Virginia Polytechnic Institute and State University, Blacksburg, VA 24061–0111, pp. 2364–2367, Industrial Electronics, Control, and Instrumentation, 1993. Proceedings of the IECON '93, International Conference on Maui, Hawaii Nov. 15–19, 1993; XP010109392.

Chen et al, "Measure of Molecular Mass of Polyacrylamide with Intrinsic Viscometry", Technology Supervision in Petroleum Industry 2001, vol. 1, pp. 22–24 and English language translation.

*Primary Examiner*—Hezron Williams
*Assistant Examiner*—John C Hanley
(74) *Attorney, Agent, or Firm*—Nixon & Vanderhye P.C.

(57) ABSTRACT

The present invention relates to a method and apparatus of determining the rheological properties of a polymer flowing in a conduit. The invention provides a method of characterising a polymer under test, comprising: Detecting acoustic emissions from said polymer flowing in a conduit to provide acoustic emission data, comparing the acoustic emissions data obtained against acoustic emission data from a polymer, or a series of polymers, of known characteristics, and thereby characterising the polymer.

12 Claims, 7 Drawing Sheets

U.S. PATENT DOCUMENTS

| | | |
|---|---|---|
| 4,339,944 A | 7/1982 | Abts et al. |
| 4,392,374 A | 7/1983 | Liebermann |
| 4,779,452 A * | 10/1988 | Cohen-Tenoudji et al. 73/54.41 |
| 4,869,233 A * | 9/1989 | Stulen et al. ............. 126/374.1 |
| 4,979,124 A | 12/1990 | Sachse et al. |
| 5,148,405 A | 9/1992 | Belchamber et al. |
| 5,302,878 A | 4/1994 | Soucemarianadin et al. |
| 5,317,908 A * | 6/1994 | Fitzgerald et al. ......... 73/54.26 |
| 5,433,112 A * | 7/1995 | Piche et al. .................... 73/597 |
| 5,459,677 A | 10/1995 | Kowalski et al. |
| 5,568,400 A | 10/1996 | Stark et al. |
| 6,439,034 B1 * | 8/2002 | Farone et al. ............... 73/54.24 |

* cited by examiner

VISCOSITY MEASUREMENT

This is the US national phase of international application PCT/GB01/05771 filed 21 Dec. 2001, which designated the US.

The present invention relates to a method of determining the rheological properties of a polymer flowing in a conduit. The method is particularly suitable for determining the viscosity of the polymer, and other properties such as the molecular structure or chemical composition of the polymer can also be determined. Also provided is an apparatus for carrying out the method.

Polymers are generally manufactured using chemical synthesis reactions between one or more basic molecules, known as monomers, which react together under favourable conditions to form a polymer, which consists of long chains of the monomers joined together.

In general, in polymer manufacturing processes, the composition of the polymer chain (i.e. the molecular structure of the polymer) is carefully controlled by adding the monomer(s) to the reaction mixture at a carefully controlled rate. Where there are two or more monomers, these are added to the reaction mixture in strictly controlled proportions to one another e.g. in a constant ratio. It is also necessary to maintain the reaction conditions at the correct levels in order to control the rate at which each monomer reacts with the other monomer(s) and hence control the resulting molecular structure. Reaction conditions include temperature, pressure, rate of mixing, rate of shear etc. Of course, even when a single monomer is used, such as in the manufacture of polyvinyl chloride (PVC) or polyethylene, the molecular structure is also affected by the reaction conditions because the length of each polymer chain can vary and the chains can be branched or unbranched to varying degrees. This degree of "branching" of the polymer chain affects the physical properties (e.g. density and strength) of the polymer product.

Clearly then, the molecular structure of a polymer product must be carefully controlled during polymerisation reactions. However, measurement of the polymer properties during reaction is extremely difficult. Properties such as the viscosity or melt flow index (MFI) of the polymer when melted are very good indicators of the molecular structure, and hence the physical and chemical properties of the polymer. However it is necessary either to take samples of polymer from the reactor in order to carry out conventional measurements of viscosity and MFI in the laboratory, or in some cases an "on-line" rheometer may be fitted in the outlet pipe from a reactor.

Sampling techniques are time-consuming and introduce delays in obtaining the information—therefore this is not an effective way of continuously controlling the reaction since by the time the results are analysed and appropriate action taken, the reaction conditions will be different and some of the polymer product may already be adversely affected.

On-line rheometers generally work on the principle that a small amount of molten polymer is syphoned off into a smaller "by-pass" duct, and the rheological properties of the polymer, such as the MFI or viscosity can be measured. The rate of flow of the polymer in the by-pass line at a given pressure (or load) is dependent on the viscosity or MFI of the polymer, at a known shear rate. Hence on-line viscosity or MFI can be measured. Unfortunately, though, this form of measurement is theoretically complicated and involves the use of sophisticated and expensive equipment for example transducers may be needed to measure pressure and flow-meters and sometimes also gear pumps are required.

Another approach to this problem is found in GB 2 038 051, published in 1980, which discloses the idea of an "acoustic probe" which can be immersed in polymerising mixture in the reactor and used to monitor the rheological properties of the polymer. The probe was intended to pick up sound-wave signals from the polymer flowing inside the reactor, and amongst other things, it was intended to help to monitor the viscosity of the polymer by correlating viscosity with the logarithmic decrement of sound-wave oscillations.

However, in order to pick up useful measurements, the probe needed to be positioned in a region of polymer flow, such as near to the stirring device in the reactor. This creates practical difficulties in that the probe is liable to be damaged and is difficult to maintain in position in the reactor. Any device which has to be immersed in the polymer melt itself is inherently difficult to operate and is generally best avoided wherever possible. Furthermore, measurement of polymer properties in the reactor has problems because the properties in the reactor are not necessarily the same as the properties of the final polymer produced.

In Esbensen et al (1998); "Acoustic chemometrics; from Noise to information", Chemometrics and and intelligent laboratory systems 44 (1998) 61–76, an acoustic device is described for use with particulate materials.

Viewed from one aspect, the invention provides a method of characterising a polymer under test, comprising:

detecting acoustic emissions from said polymer flowing in a conduit to provide acoustic emission data, comparing the acoustic emissions data obtained against acoustic emission data from a polymer, or a series of polymers, of known characteristics, and thereby characterising the polymer.

Preferably, said method enables a rheological property of a polymer under test to be determined, by comparing the acoustic emissions data against such data from a polymer, or a series of polymers, of known rheological properties, and thereby determining the rheological property of said polymer under test.

It will be appreciated that in order for the polymer to flow and a meaningful evaluation of its properties to be deduced, it will generally be necessary to melt the polymer so that it is no longer in solid form. Hence reference to a "polymer flowing" as used herein should be understood in general as reference to a molten polymer which is able to flow.

Thus, the invention is based on the discovery that it is possible to determine the characteristics, preferably the rheological properties, of a polymer flowing in a conduit, without the need for expensive and complex equipment and without the need to immerse a probe or sensor in the flowing fluid. It has furthermore surprisingly been found that the acoustic emissions from a particular polymer are sufficiently characteristic for each different type of polymer to be identified. Also, for any given polymer for which molecular structure may differ from batch to batch or over time during continuous processing, this variation can be monitored. In fact, the composition of the polymer can be determined from the acoustic emission data of that polymer.

The composition of the polymer can of course be inferred or determined from any values of the rheological properties obtained, e.g. from the viscosity of the polymer, but it will be appreciated that direct comparison of emission data alone from polymers of known identity can also be made. Thus, in order to identify a particular polymer according to its composition, a value for the viscosity or other rheological property of that polymer need not actually be determined from the acoustic emission data in order to identify the polymer.

Thus viewed from another aspect, the invention provides a method of identifying a polymer under test, comprising:

detecting acoustic emissions from said polymer flowing in a conduit, comparing the acoustic emissions data obtained against acoustic emission data from a polymer of known identity, and thereby determining the identity of the polymer under test.

In this case, the identity of the polymer may be in the form of an accurate determination of the molecular structure of the polymer, or it may be simply be an indication of the type of polymer being produced (e.g. determining whether it is polyethylene, polypropylene or a particular co-polymer, or even the particular composition).

Rheological properties as referred to herein include viscosity (intrinsic, extrinsic, kinematic or dynamic viscosity), shear-strain or shear-stress, melt flow index (MFI) or any other rheological parameter which is characteristic of a given polymer. [The term "rheological property" as used herein however does not include parameters such as flow rate or flow velocity, temperature, pressure, load or pressure drop which may or may not be determined incidentally when the method of the invention is carried out. These and many other properties of a fluid flowing in a conduit are not "rheological properties" within the meaning of the invention since they are not characteristic of any given fluid or polymer].

It will be appreciated by those skilled in the art that rheological properties are generally determined for a given fluid at a pre-determined or preferably constant value of the non-rheological properties. Thus for example the viscosity of a fluid may vary with temperature, flow rate, pressure etc., hence a value of viscosity should ideally be compared against another at a given temperature and under given flow conditions etc. Since it is the molecular weight and molecular weight distribution (MWD) which is of prime interest in controlling the properties and hence quality of the polymer product, it is a change in any of these properties which is of interest rather than measurement of an absolute value, in most cases.

In fact, the viscosity of a polymer also varies with other rheological properties, e.g. shear stress. If a graph of shear stress against viscosity is plotted for a given polymer, the shape of the curve is indicative of the molecular weight distribution of the polymer. However, by comparing the acoustic emission data obtained in accordance with the invention against emission data from known polymers under the same flow conditions e.g. at a given temperature, flow rate etc., complex calculations of the polymer properties can be avoided and the identity and/or rheological properties of a polymer can be determined directly.

It is therefore preferred that the method of the invention be performed by detection of acoustic emissions from the polymer at a pre-determined flow rate, pre-determined pressure and/or a pre-determined temperature. In particular, it is advantageous to control the flow rate of the polymer in order that the shear rate of the polymer is known. For example, the flow rate of the polymer may be controlled over a pre-determined range corresponding to a desirable shear rate range for the polymer under test. In this way, it is possible to optimise the flow rate to provide a shear rate in which the best possible distinction in measured characteristics (e.g. viscosity) is obtained for any given polymer. The skilled person will readily understand how to determine the optimal flow rate range by carrying out simple tests at different measured flow rates. The optimal flow rate range for any given polymer will depend on the characteristic of the polymer which is to be determined.

Apparatus to measure the temperature of the polymer in the conduit is well-known in the art and may for example be a thermocouple device contained in or placed on the conduit. Alternatively, the temperature of the conduit in which the polymer flows can be measured either at or near to the point at which the acoustic sensor is located, or at another convenient point e.g. at the nozzle outlet of an extruder. All that is required is that the temperature should be pre-determined at a given point which is indicative of (i.e. related to or dependent on) the temperature of the polymer at the point where the acoustic emissions are being detected.

In many cases, the temperature at which a polymer melts will be significantly above ambient temperature. Typically, temperatures of a polymer melt may exceed 100° C. and may be as high as 125 to 250° C. or higher. The sensor means used to direct the acoustic waves emitted from the polymer must therefore in many applications be able to withstand these high temperature.

A typical acoustic sensor means for use in accordance with the invention would be an accelerometer. Accelerometers are known acoustic sensor devices and are widely available, for example of the type manufactured by Brüel and Kjær in Denmark. Where high temperatures need to be withstood by the sensor means, this should be borne in mind when selecting a suitable device. Accelerometers for example can be manufactured to withstand temperatures up to and above 250° C. and the technology to do this is well known to manufacturers of accelerometers.

The conduit in which the polymer flows may take any form. Preferably however the conduit is a pipe e.g. a cylindrical pipe which may be made of any suitable material. Steel is typically used in polymer production processes but other corrosion-resistant materials may be used. The material of the conduit should however be suitable to allow acoustic waves to be well conducted in order to be detected outside the conduit. Hence acoustically conductive materials, especially metals such as steel are preferred. The acoustic sensor means must be placed in acoustical contact with the conduit.

In order to enhance the acoustic emissions from the polymer as it flows, it is preferable to cause a disturbance in the flow of the polymer in the conduit. For example, the pipe may be modified in some way to alter the flow characteristics, especially to cause a sudden change in the flow. Thus, a structural detail may be provided in the conduit in order that the conditions of flow change, at or near the portion of the conduit in which acoustic emissions are detected. It has been found that the presence of a constriction in a pipe is particularly suitable. The diameter of the constriction is not crucial but it must be sufficiently small relative to the diameter of the conduit to allow the necessary degree of turbulence to occur. An orifice plate of the type routinely used for flow measurement is an ideal way of providing a constriction in a pipe. Other forms of structural detail which may be used to create turbulence include, but are not limited to, a bend (e.g. 45° or 90°) in the conduit, the presence of a valve or other choke mechanism. A sudden increase in pipe diameter may also be suitable.

Where the polymer exits the reactor in molten form (e.g. low density polyethylene) the conduit may be an exit pipe directly from the reactor, or it may be a by-pass pipe from one of the main polymer pipelines. Where the polymer is initially in solid form (e.g. granules or powder) a melting step is needed. The acoustic rheometer in accordance with the present invention may be used in a similar manner to existing or known rheometers i.e. it is suitable for use in any form of conduit and therefore it may simply replace an existing rheometer. For example, existing and known rheometers such as online rheometers are often situated in a by-pass line from an extruder or they may be placed on an extruder directly. For example, the conduit in accordance with the invention may be associated with a single or plural screw extruder.

As mentioned above, flow conditions are also preferably kept at a pre-determined level in order to allow effective comparison of acoustic emission data with data from known polymers. Hence, preferably the flow rate of the polymer in the conduit is measured and/or monitored at or near the point at which the acoustic sensor is positioned. Flow rates can conveniently be measured by any method known in the art i.e. by any flowmeter, but it may in some instances be convenient also to measure flow rates by acoustic means, e.g. by detecting the Doppler shift etc. However, in order to measure the flow rate in accordance with such apparatus, it will be noted that a sound-wave (ultrasound >25 kHz) source other than the polymer flow itself must be present, as this technique depends on detection of ultrasound waves which are reflected off the flowing fluid.

This differs from the detection method of the present invention which relies on passively emitted acoustic waves from the polymer itself. However, there is no reason why any necessary flow rate measurements cannot be taken using a separate ultrasound sensor means in sender-receiver mode, and utilising this ultrasound sensor means to pick up the reflected ultrasound for flow rate measurement.

Where the polymer is passing through a pipe or extruder, the pressure in the extruder or pipe is also preferably measured and/or maintained at a pre-determined level.

Figure 5:
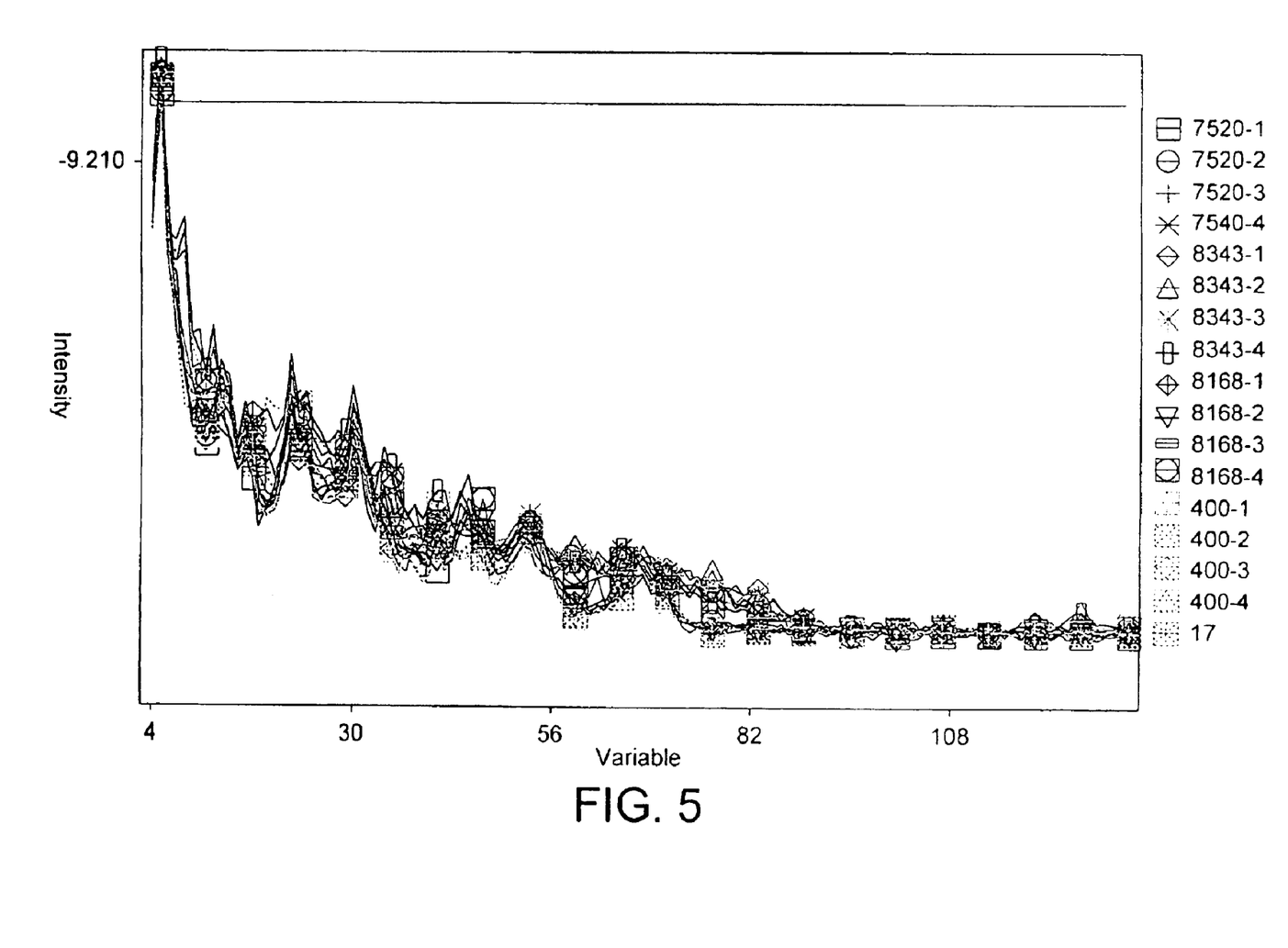
FIG. 5 shows an acoustic spectrum in the frequency range 0–25 kHz, for each of the four different polymers as described in Example 1.

As explained above, the invention relies on the principle that movement of the polymer, for example through a constriction in the conduit, causes the polymer-conduit assembly to produce vibrational acoustic emissions, which can then be detected. One preferred way in which the detection takes place is to generate an acoustic spectrum which typically may take the form of a graphical representation of the emitted acoustic waves. An example of an acoustic spectrum is shown in FIG. 5. However, in its simplest form, an acoustic spectrum generated in accordance with the invention could take the form of a plot of amplitude on the Y axis against frequency on the X axis called a "power spectrum".

The acoustic spectrum for any given polymer acts as a multivariant "fingerprint" for that polymer, since it is different from the spectra of other polymers (and other fluids generally) flowing at the same point in the conduit under the same flow conditions. Hence, in accordance with the invention, a polymer can be identified by comparing its acoustic spectrum against acoustic spectra of known polymers until a match is found. Where the rheological properties of that polymer are also known, the rheological properties of the polymer under test can also be determined from a comparison of the acoustic spectra.

If the acoustic spectra are recorded e.g. in electronic form or in any other form of searchable database, rapid comparison of data can be carried out e.g. by computer analysis, and swift matches for the identity of a polymer and/or the rheological properties of a polymer can be found. The speed of response which can be achieved using computer processing techniques means that data obtained from the detection of acoustic emissions can be analysed in a database, and values for rheological properties or the identity of a polymer can be determined in a matter of seconds, or even milliseconds. Hence the method of the invention is particularly advantageous for on-line monitoring of properties of polymers and this can be used to facilitate process control.

Thus in a preferred aspect, the invention provides a method for the determination or on-line measurement of the rheological properties of a polymer, comprising:

detection of acoustic emissions from said polymer flowing in a conduit, and comparison of the acoustic spectrum generated against the acoustic spectra of polymers of known rheological properties, whereby to determine the rheological properties of the polymer under test.

The range of acoustic emissions detected may be anywhere in the acoustic frequency range of 0 to about 25 kHz.

As explained above, the acoustic emissions detected can provide a set of data which can provide a "fingerprint" of the polymer concerned.

In a simple case, acoustic emission spectra can provide a set of numbers which is characteristic of the particular polymer produced. This set may be compared with a corresponding set which is known to relate to acceptable products (e.g. from previously produced product). By determining whether the numbers are sufficiently similar (e.g. within previously specified tolerances) it may be determined whether the fluid is itself acceptable. It will be appreciated that these numbers relate indirectly, but unambiguously to molecular weight and molecular weight distribution, although absolute values need never be found for these parameters. Nevertheless, it may in practice also be useful to do so.

The previously acquired sets of acoustic emission data may have been obtained by making similar measurements of known polymers having desired characteristics. For example, sets of data may be obtained for each polymer which it is desired to produce corresponding to the ideal conditions for producing that polymer.

Close similarity between the measured data and one of these previously acquired sets of target data may then be used to identify the polymer concerned and/or to determine whether a desired polymer is being produced with the correct characteristics.

It will be appreciated that this comparison could be performed in numerous ways and in the simplest case useful information could be obtained even from visual comparisons of plots of the various data sets. However, these comparisons are preferably automated. In practice this means that the comparisons are carried out by a computer.

Numerous known computational techniques may be used to perform the analysis, but it is has been found that multivariate calibration is particularly effective and accurate (see Martens and Naess 1989 "Multivariate Calibration" published by John Wiley, Esbensen (1998)). Thus, a latent variable corresponding to an optimal linear combination of the measured frequency data may be introduced. The data are then redefined in relation to this latent variable.

In a particularly preferred form of the invention, Principal Component Analysis (PCA) of the acoustic emissions data is used for classification of new samples in relation to old samples of known properties. The raw data may be subjected to preprocessing such as e.g. transformation, centering, smoothing or scaling. Subsequently, from a set of samples ("calibration set") of known properties a data subspace is empirically identified into which the test sample data points may be projected. This subspace is described by a set of "latent variables", spanning individual axes in the subspace and is denoted the "model" of the given class of samples. The number of latent variables are then empirically found as those needed to give representative information related to flow properties of the fluid in question based on casual knowledge by the operator. It will be noted that it is not necessary to run any transformation to align with rheological parameters.

If a visual evaluation is desired, a plot of the data may be produced where the axes are given by the latent variables, and where new samples are compared to the set of known samples, and to limiting values based on the same samples. For a mathematical evaluation (classification) upper and lower limiting values may be defined for the value of the latent variables, and for residuals of the raw data after projecting into the subspace an upper limiting value is defined. Then new samples may then be classified according to these limiting values. This approach has been termed the SIMCA approach, as referred to in Esbensen 1998 and numerous other references herein.

Typically, when using PCA, the latent variables are defined by the eigenvectors of the (n×k) matrix e.g. where n is the number of samples in the calibration set and k is the number of values measured for a given variable. Each sample in the calibration set, and future test process samples, may then be described by their score values along the individual latent variables thus defined.

By calculating the correlation of the latent variable with polymer property parameters like MWD, MFR (melt flow rate), etc. one will obtain knowledge of along which direction these parameters have their largest variability in the latent variable data space. This information may be compared to the position of the individual samples in the same data space, to evaluate their score in relation to the different parameters.

By calculating the correlation of the latent variable with processing parameters like reactor temperature, reactor feed compositions etc., one will obtain knowledge of along which direction these parameters have their largest variability in the latent variable data space. This information may be compared to the position of the individual samples in the same data space, to evaluate their score in relation to the different parameters, and it may be used to estimate how process parameters should be changed to change the positioning of the product in the latent variable space to have the selected flow properties represented by the acoustic emission data values.

It is particularly preferred for the method to be implemented using a computer arranged to display a score plot representing the data at least substantially in real time. In this way, as new data is acquired and new plots are added to the score plot, changes in the fluid (polymer) characteristics may be followed. It is helpful for an indication to be provided on the display of where the boundaries between acceptable and unacceptable points lie, for example based on statistical quantities. The indications may be a boundary line in the form of an ellipse. Points falling outside the boundary correspond to unacceptable product.

As discussed above, the score may be evaluated in relation to different parameters and so it is possible to correlate the position of a point outside the boundary with the corresponding deficiency in its properties. This information may then be used to enable appropriate corrective action to be taken by a plant technician. For example, the previously acquired data sets could include data corresponding to known incorrect settings for the desired product from which previously determined corrective action may be taken. Such previous data sets could have been deliberately produced or they could be learned automatically from analysis of previous operations of the plant. Alternatively the plant may be adjusted in an iterative manner based upon the nature of the deviation of the measured data sets from the desired data set.

In particularly preferred forms of the invention, means is provided to automatically adjust the operating conditions of the plant in order to ameliorate the deficiency. Of course, there need not be a display for this to be effective—the "ellipse" may simply be a defined volume of data space.

Another advantage of this form of the invention is that even if a product is determined to be acceptable, it is possible to monitor variations in where points are plotted (or located in data space) in order to determine trends which may be used to anticipate future deficiencies and to take corrective action before they occur. Preferably this is also implemented automatically.

In this context PCA represents one way of identifying the latent variables. However, it will be appreciated that any other mathematical method involving linear or non-linear transformation of the relevant process data into a set of latent variables may be used. Examples of other methods are Partial Least Squares Regression (PLSR), Neural Networks (NN) and curve fitting of the pressure data or preprocessed pressure data to a curve of selected exponential degree.

A particularly preferred aspect of the invention is to use the acoustic emission data for quantification of selected polymer properties, e.g. MFR or MWD. Again the raw data may be subject to preprocessing such as e.g. transformation, centering, smoothing or scaling. From a set of samples ("calibration set") of known properties it is then possible empirically to identify a mathematical relation (the "model") to quantify the selected properties based on the preprocessed pressure. This model may be any linear or non-linear relation defined by methods like Principal Component Regression (PCR), Partial Least Squares Regression (PLSR), Neural Networks (NN), etc.

When using PCR and PLS, latent variables may be identified in a modified form closely related with PCA (above), and then a linear regression model is developed between the polymer property and this type of latent variable. In the same way as when doing classification above, the score values in the latent variable space may then be used for visual and mathematical evaluation. Correlation between the latent variables and process parameters may be used to identify how the process parameters should be changed to adjust the selected property of the polymer being produced.

It will be appreciated from the foregoing that the present invention is useful in the field of polymer production and so acoustic emission detection means is preferably situated on-line and may be associated with an extruder used in such a context. Polymer may be fed from the extruder directly into a suitably modified conduit for acoustic emissions to be detected, e.g. by means of a bypass. Because of the speed of operation and the improved accuracy of the method of the invention, if the properties of the polymer are as desired, this will be known much more speedily than in the prior art system. Furthermore, it is also possible to determine more quickly if the measured characteristics are not as required and then to adjust the operating conditions of the reactor accordingly in order to obtain the desired characteristics. Consequently, wasted production may be greatly reduced.

It is possible to apply the method of the present invention either only when the reactor is first set up for a given production run, or at occasional intervals as required by quality control. However, since the method may operate automatically it is particularly preferred that regular and comparatively frequent measurements be made, say around every 10 minutes.

Polymer producing plants are normally operated continuously and if it is desired to change from production of one polymer to another this is done without closing down the plant. Instead, the reactor operating conditions are adjusted in order to change the polymer thereby produced and fed to the extruder. Thus, preferably the method of the invention is used to obtain data which is used to monitor the transition between products. Since in the preferred forms of the invention the data acquisition and subsequent comparison steps are carried out by computer, this may be done rapidly. Consequently, the transition may be effected more smoothly and quickly than in the prior art and moreover the operator can determine more quickly when the desired product starts to be produced. It will be appreciated that this significantly reduces the amount of wastage associated with operation of the reactor therefore a significant advantage in terms of saving time and materials and thereby costs.

The invention also provides an apparatus, also referred to herein as an acoustic rheometer, for carrying out the method of the invention, and the use of the acoustic rheometer to control a polymerisation reaction. Thus viewed from a further aspect the invention provides an apparatus for characterising a polymer, comprising:

a) an acoustic sensor capable of detecting acoustic emissions from the polymer and thereby generating a signal;

b) means for comparing the signal against acoustic emissions data from polymers of known characteristics. This data may for example be stored in a computer memory either provided within the apparatus or remotely.

The invention also provides the use of an acoustic rheometer comprising a) an acoustic sensor capable of detecting acoustic emissions from a polymer;

for controlling a polymerisation reaction producing said polymer. Preferably, in this aspect, the acoustic rheometer further comprises means for comparing the signal against acoustic emissions data from polymers of known characteristics, as defined above.

Preferably, the apparatus is adapted for determining the rheological properties of a polymer, comprising:

a) an acoustic sensor capable of detecting acoustic emissions from the polymer and thereby generating a signal;

b) means for comparing the signal against acoustic emissions data from polymers of known rheological properties whereby to determine a value for the desired rheological property of the polymer under test.

The apparatus may further comprise means for identifying the polymer. Preferably, the apparatus comprises an acoustic sensor which is capable of detecting vibrational acoustic emissions in the interval 0–25 kHz.

The acoustic sensor may be as described above. The means for comparing the signal (referred to hereinafter as "comparison means b)") may if necessary or desired comprise means for amplifying or processing the signal from the acoustic sensor. For example the comparison means b) may be a computer which in turn may be connected e.g. to a signal amplifier or preprocessor. The computer will preferably be loaded with suitable software. Conveniently, the comparison means b) may be provided by a package such as the Multi-Channel Spectrum Analyser available from Applied Chemometrics Research Group (ACRG), Tel-Tek, Porsgrunn, Norway.

The apparatus of the invention is set up such that the acoustic sensor means is positioned in acoustic contact with (preferably touching) the conduit through which a polymer can flow. The conduit is preferably a straight segment of a pipe and preferably this has a structural detail as hereinbefore described. The acoustic sensor means is therefore positioned whereby to detect acoustic emissions from the flowing polymer as it passes through the structural detail in the pipe.

It has been found in particular that the acoustic sensor means can be placed in a variety of positions in relation to the conduit in order to successfully determined rheological properties of a polymer. For example, it could be placed before or after the structural detail e.g. within about 5–20 cm or 5–10 cm of the structural detail (relative to the direction of flow) but preferably it should be placed before the structural detail. Alternatively it could be positioned at the position of the structural detail itself, which is particularly preferred.

The invention also extends to a polymer production plant incorporating the method or apparatus of the invention as set forth above and also to polymer products thereby produced.

Certain embodiments of the invention will now be described, by way of example only and with reference to the accompanying drawings in which.

Figure 1:
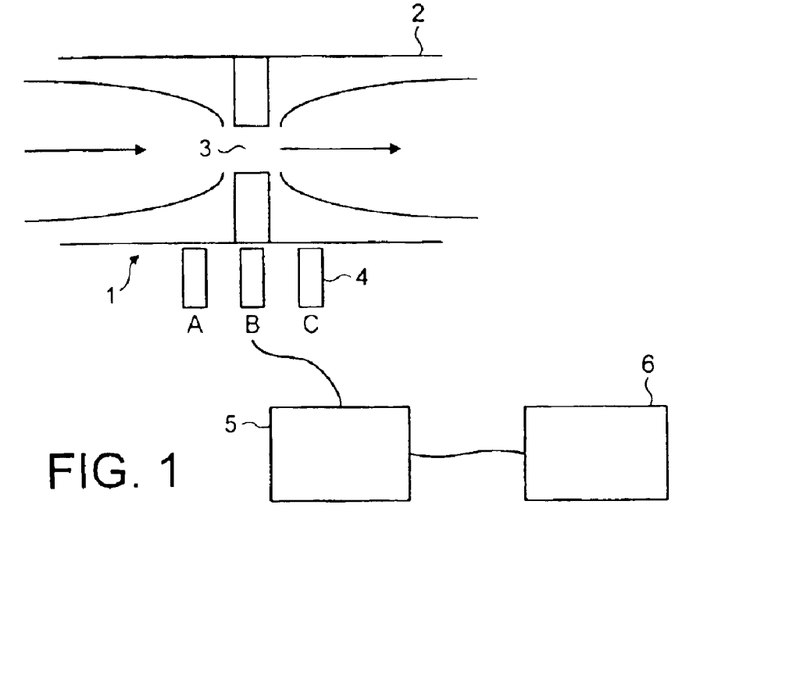
FIG. 1 is an acoustic rheometer according to the invention.

FIG. 1 shows an ultrasound rheometer for operation in accordance with the invention. Typically, the polymer melt leaving the polymerisation reactor will be processed through an apparatus 1 which consists of a conduit 2 with a constriction 3 allowing the polymer to pass through. The acoustic sensor means 4 e.g. an accelerometer may be placed in any one or more of positions A (before the constriction), B (at the constriction) or C (after the constriction). The accelerometer 4 detects acoustic emissions from the polymer flowing through the apparatus 1 and generates an acoustic spectrum which is characteristic of the polymer. The signal is amplified by an amplifier/preprocessor 5 and data analysis is carried out by a computer 6 or other suitable means. Data analysis can for example be carried out by mulitvariate analysis techniques such as principle component analysis (PCA) or partial least squares (PLS). Information on the viscosity, molecular structure, MFI and other polymer properties can then be calculated by comparison with information from known polymers.

Figure 2:
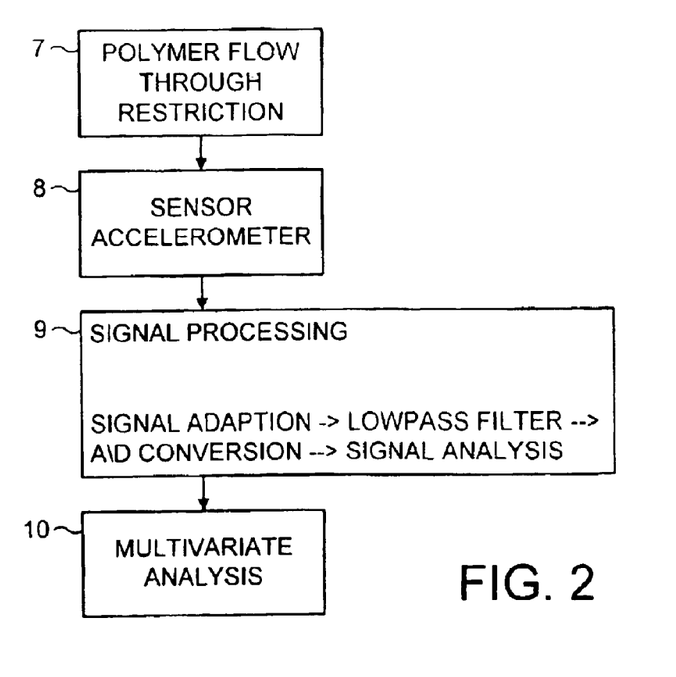
FIG. 2 is a schematic flow diagram showing the data path for analysis of the acoustic emissions data.

FIG. 2 is a schematic flow diagram showing the data path from the acoustic emissions (vibrations) generated by the polymer and how that data is analysed numerically. Box 7 represents polymer flow through the constriction in the conduit, from which the acoustic signal is detected by the sensor accelerometer 8. Box 9 represents signal processing by adaptation of the signal through a lowpass filter and analog-digital conversion to allow analysis of the signal. Multivariate analysis of the signal data is then carried out, as represented in box 10.

Figure 3:
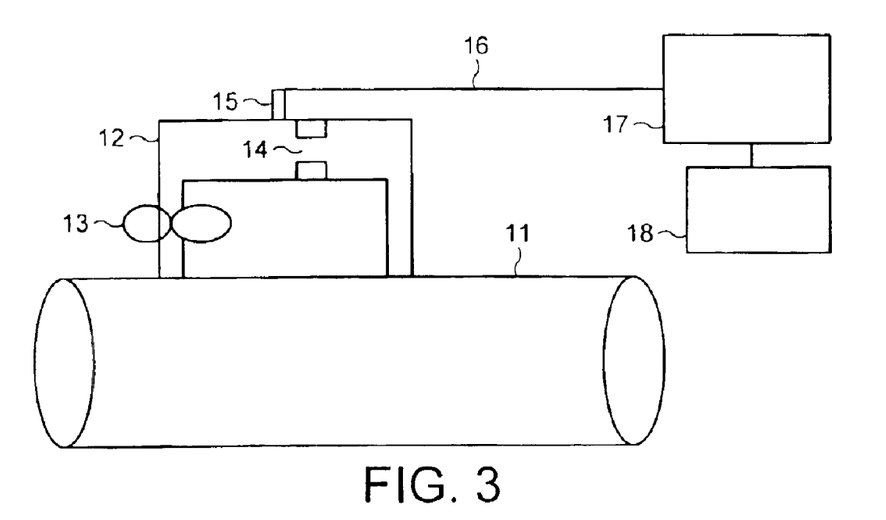
FIG. 3 is a diagram of one possible configuration of an acoustic rheometer according to the invention.

FIG. 3 shows one possible configuration for the acoustic rheometer mounted on a by-pass from an extruder. The extruder barrel 11 is shown with the by-pass line 12 leading from it and round the by-pass "loop" back into the extruder 11. Polymer is pumped round the by-pass pipe 12 by means of a gear pump 13, piston, or any other suitable device for generating flow, and through a constriction 14 in the by-pass pipe. The acoustic sensor means 15 is placed outside the pipe in acoustical contact therewith, and leads 16 transmit the signal to an amplifier 17 and then to a personal computer 18 which is capable of analysing the data by means of multivariate analysis (MVA).

Figure 4:
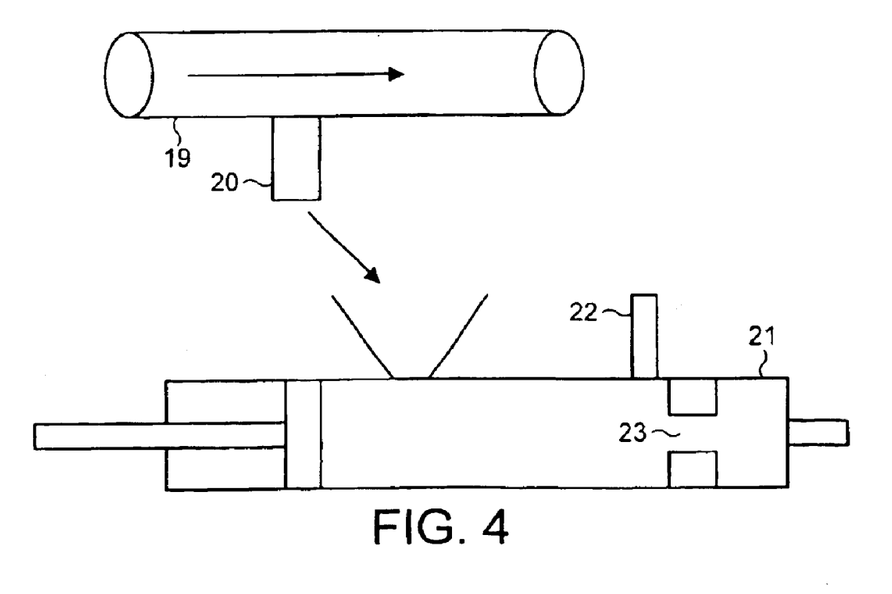
FIG. 4 is another diagram showing a different possible configuration of an acoustic rheometer according to the invention.

FIG. 4 shows another possible configuration for an acoustic rheometer. The polymer process flow from the polymerisation reactor is in powder form and is transported through pipe 19 from the reactor. A portion of the polymer is drawn off from the main flow pipe at a sampling point/system 20 and passed through a single screw extruder 21 or any other suitable device where it is heated and melted to allow it to flow. An acoustic sensor means 22 is placed in acoustical contact with the single screw extruder pipe at a point before where the polymer flows through a constriction 23. The signal detected by the acoustic sensor means 22 is transmitted to a data analysis unit such as a computer (not shown).

EXAMPLE 1

Comparison of 4 Different HDPE Resins using Acoustic Rheometer

The aim with this study was to compare the acoustic spectrum recorded as described in the patent with viscosity data obtained using a conventional rheometer (plate—plate dynamic rheometer; Rheometrics dynamic spectrometer, RDA-II) For this purpose 4 commercial HDPE (high density polyethylene) polymers manufactured by Borealis were chosen:

HE8168, HE8343, LE7520, LE0400

Viscosity data obtained by the dynamic rheometer (at 190° C.) is shown in table 1 below:

TABLE 1

Viscosity vs. shear rate at 190° C.

viscosity (Pa · s) at different shear rates

| shear rate | polymer LE7520 | LE400 | HE8343 | HE8168 |
|---|---|---|---|---|
| 25 | 511 | 1986 | 3793 | 860 |
| 38 | 419 | 1516 | 2973 | 857 |
| 50 | 368 | 1269 | 2534 | 855 |
| 74 | 306 | 985 | 2017 | 840 |

The experimental setup for the rheometer is shown in FIGS. 1 and 2;
The rheometer is basically a heated pipe in which a die is inserted in order to create a constriction in the pipe. At the flow inlet of the die is placed an accelerometer in order to record sound generated by the flowing polymer. Polymer is being fed by a 30 mm extruder (manufactured by company Collin GmbH)

The procedure of collecting and numerically treating the data is shown schematically in FIG. 2. (for further explanation refer to Esbensen et al (1998); "Acoustic chemometrics; from Noise to information", Chemometrics and and intelligent laboratory systems 44(1998) 61–76.

Each polymer was extruded at 4 rpm's (30, 45, 60, 90). With the die chosen for the experiments (7 mm diameter) these rates equal shear rates as shown in table 1. In table 1 (above) viscosities for the 4 polymers at the given shear rates are given based on laboratory measurements. During the experiment with the acoustic rheometer, the following data were recorded:

polymer temperature (end of extruder)
polymer pressure
Polymer temperature at the measurement point
acoustic spectrum (FIG. 5)

MVA Analysis

Figure 6:
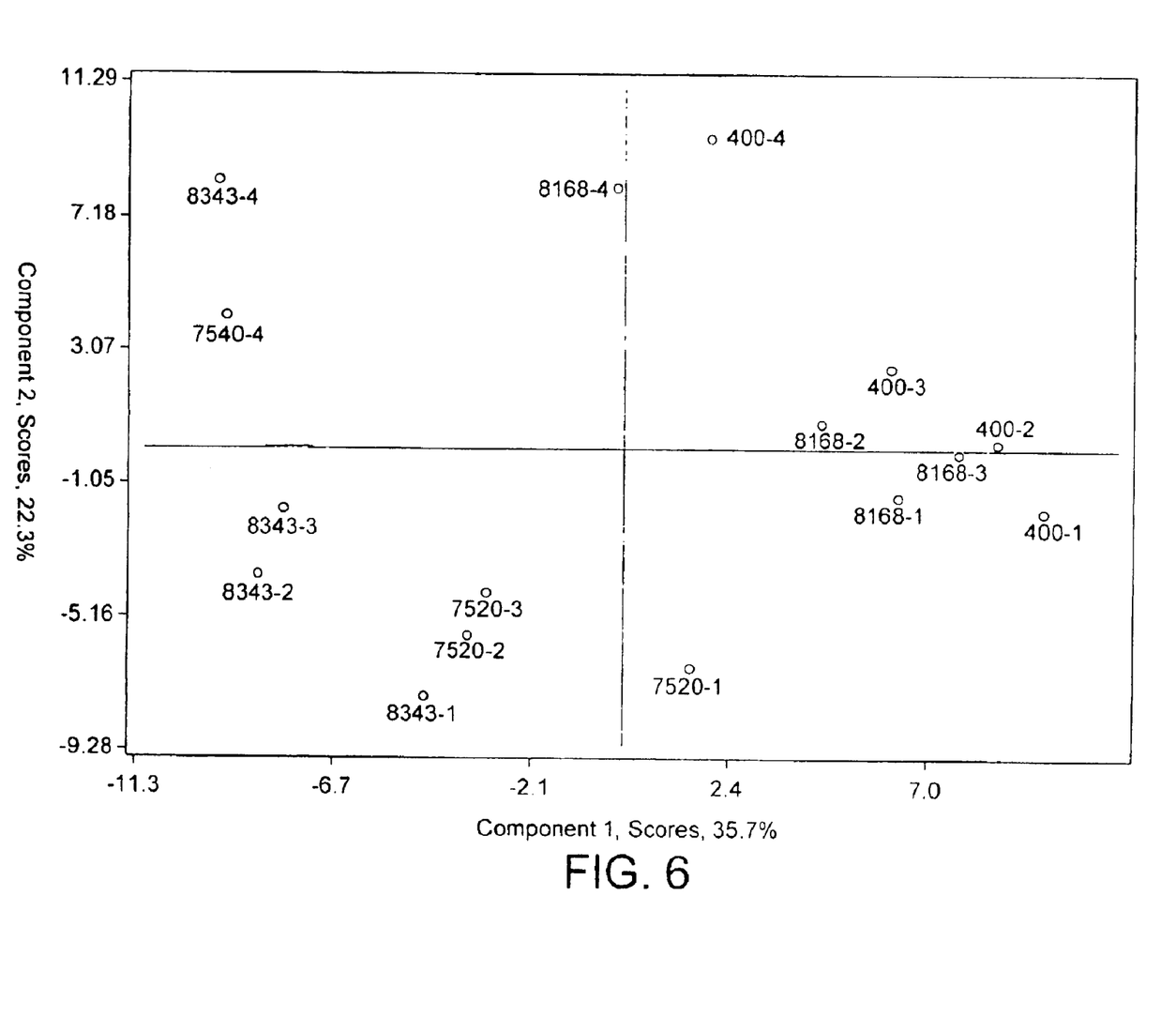
FIG. 6 shows a score plot acoustic spectrum for PCA (principal component analysis) of these four polymers. The percentage score of Component 2 (22.3%) is plotted against the percentage score of Component 1 (35.7%).

A plot of the different acoustic spectra is shown in FIG. 5 A PCA (principal component analysis) analysis is shown in FIG. 6: the scores of the first two latent variables show that the spectra are able to distinguish between the different polymers in a systematic manner.

By combining table 1 and the recorded spectra we can use PLS regression technique to study how the acoustic spectra explain the variation on viscosities at the actual shear rates.

Figure 7:
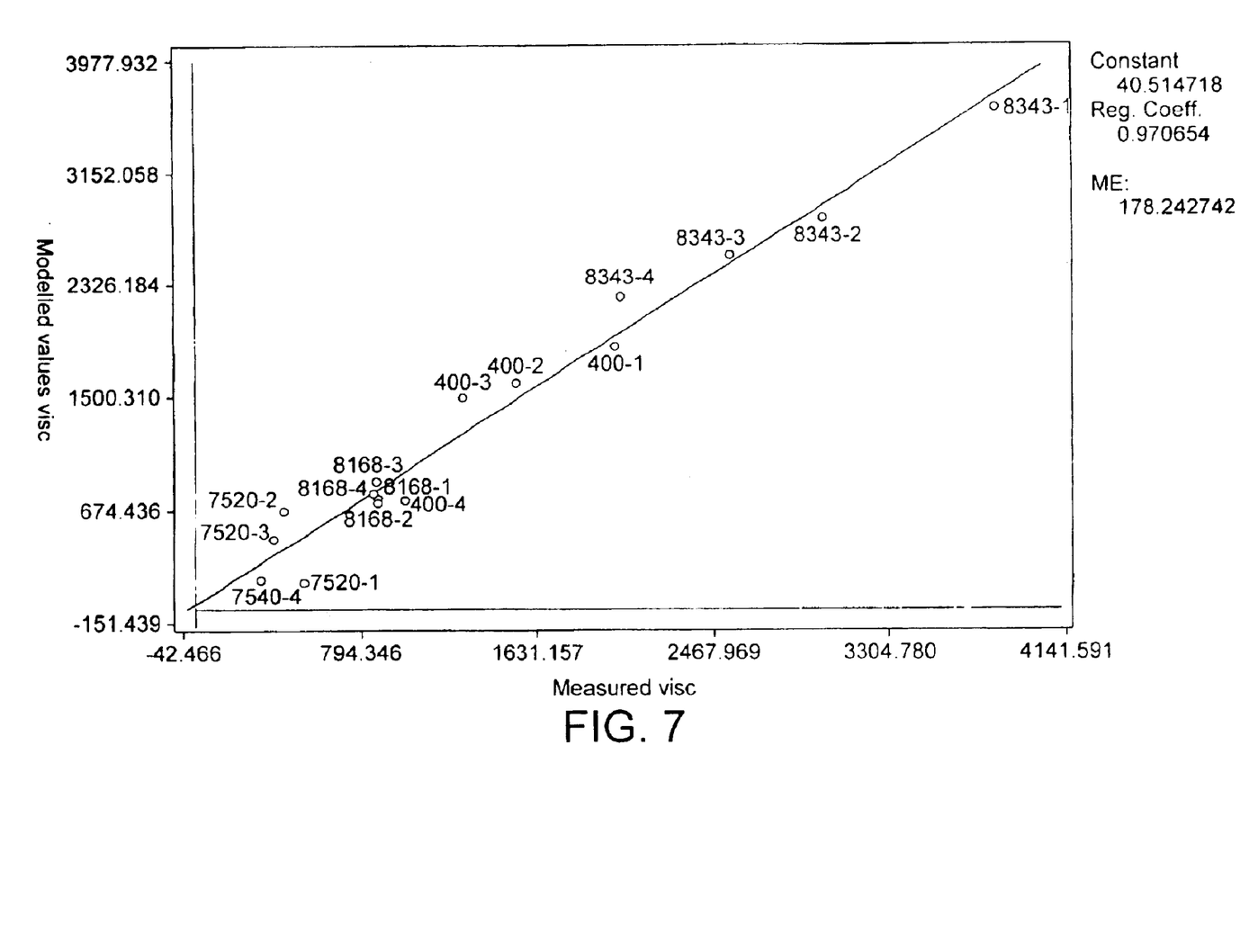
FIG. 7 shows the PLS model (partial least squares), with the viscosity of the modelled values plotted against the measured viscosity for each of the polymers.

The PLS model (FIG. 7) explains the measured viscosities by 94% in 2 comp\96% in 3 com. Cross validation reduces the explained variance to around 60%.

From this it can be concluded that the recorded spectra at a given flowrate relate to one point on the dynamic spectra curve. As done in this experiment, running at four different flow rates (or using 4 different dies) one can put the spectra together to characterize the flowcurve of the polymer.

EXAMPLE 2

Study Lot Variation Within a Single Product by Use of Acoustic Rheometer

It is well known that any commercial polymerisation process will be subject to certain variations in the molecular structure of the polymer produced. The amount of variation is usually low and in some cases difficult to quantify. Online methods are used to measure this variation in properties. The accuracy of the online rheometer will determine how well small variations can be detected and thus in the long run avoided. To test the acoustic rheometer of the invention, 4 different lots of a polymer grades with known difference in molecular structure were tested using the same setup as in example 1.

Figure 8:
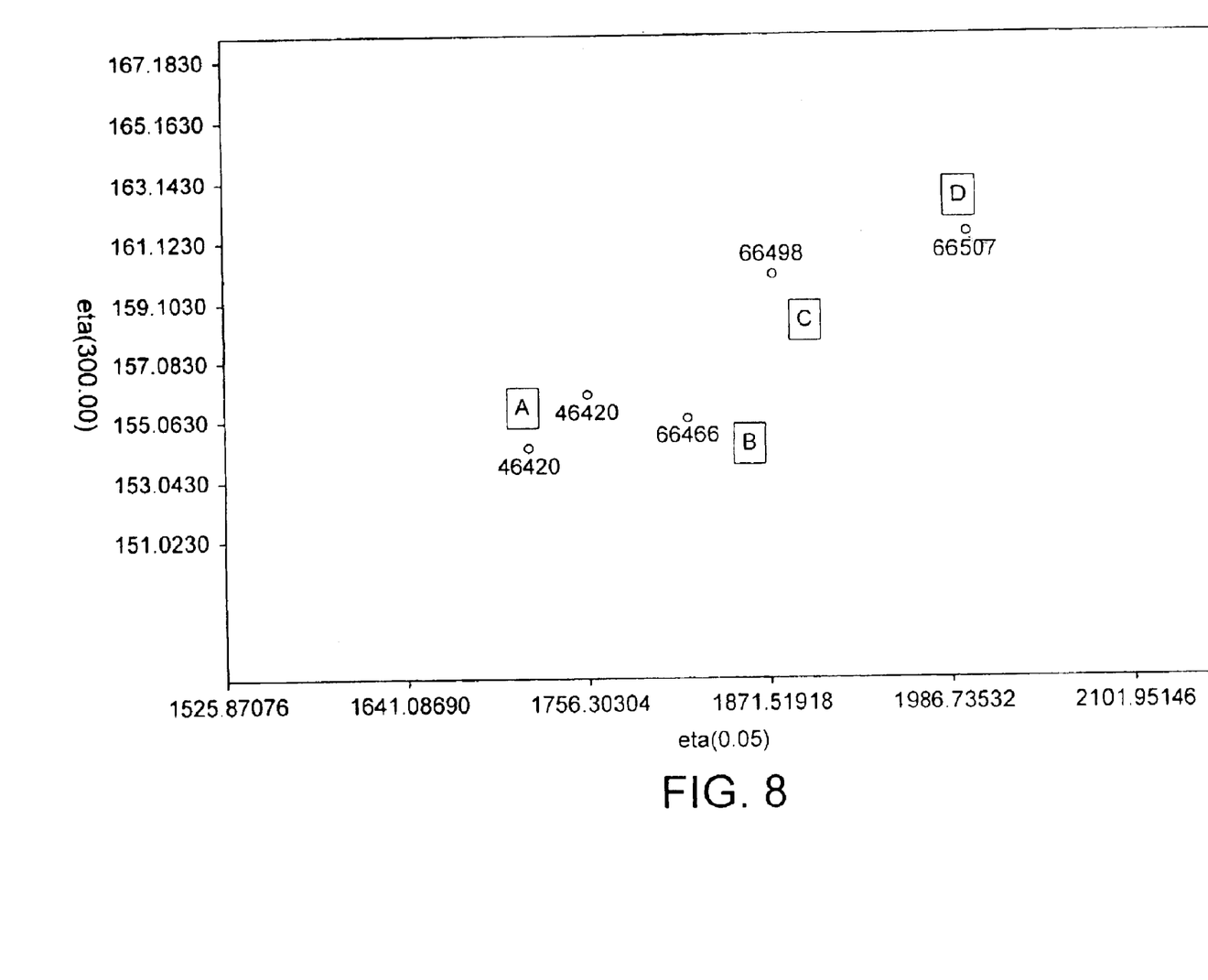
FIG. 8 shows the variation in viscosity of the four different polymers as measured by a rheometric dynamic analyser in a frequency sweep mode (190° C. melt temperature). On the Y axis the crossplot viscosity is given at 300 rad/sec and on the X axis it is given at 0.05 rad/sec.

FIG. 8 shows the variation in viscosity of the 4 lots as measured by means of a rheometrics dynamic analyser in a frequency sweep mode (190° C. melt temperature).

Each sample was extruded at 4 rates (30,50,70.100 rpm on the 30 mm extruder). Spectra in the range 0–25 KHz were recorded on a Bruel & Kjaer acclerometer (nr 4384)

TABLE 2

Part-list (high temperature equipment)

| 1 Accelerometer 250° C. | Brüel & Kjær, Denmark | Number: 4384 |
|---|---|---|
| 2 Coaxcables, 2 mm, 250° C. | Brüel & Kjær, Denmark | Number: AO 0038 |
| 1 Charge/Deltatron ampl. | Brüel & Kjær, Denmark | Number: 2646 |
| 1 UNF to BNC adapter | Brüel & Kjær, Denmark | Number: JP 0145 |
| 25 Cement studs | Brüel & Kjær, Denmark | Number: UA 0866 |
| 25 Extension connectors | Brüel & Kjær, Denmark | Number: UA 0186 |

TABLE 3

| Recording Parameters: | |
| --- | --- |
| Sampling frequency: | 50 kHz |
| Frequency range: | 0–25 kHz |
| Number of variables: | 512 fewq. + 1 Temp. = 513 variables |
| window size: | 1024 data-points |
| Transformation window type: | Blackman Harris |
| Number of replicates: | 5 |
| Recording length each replicate: | 0.02 sec. |
| Averages each replicate | 100 |
| spectrum unit: | dBV rms |

Figure 9:
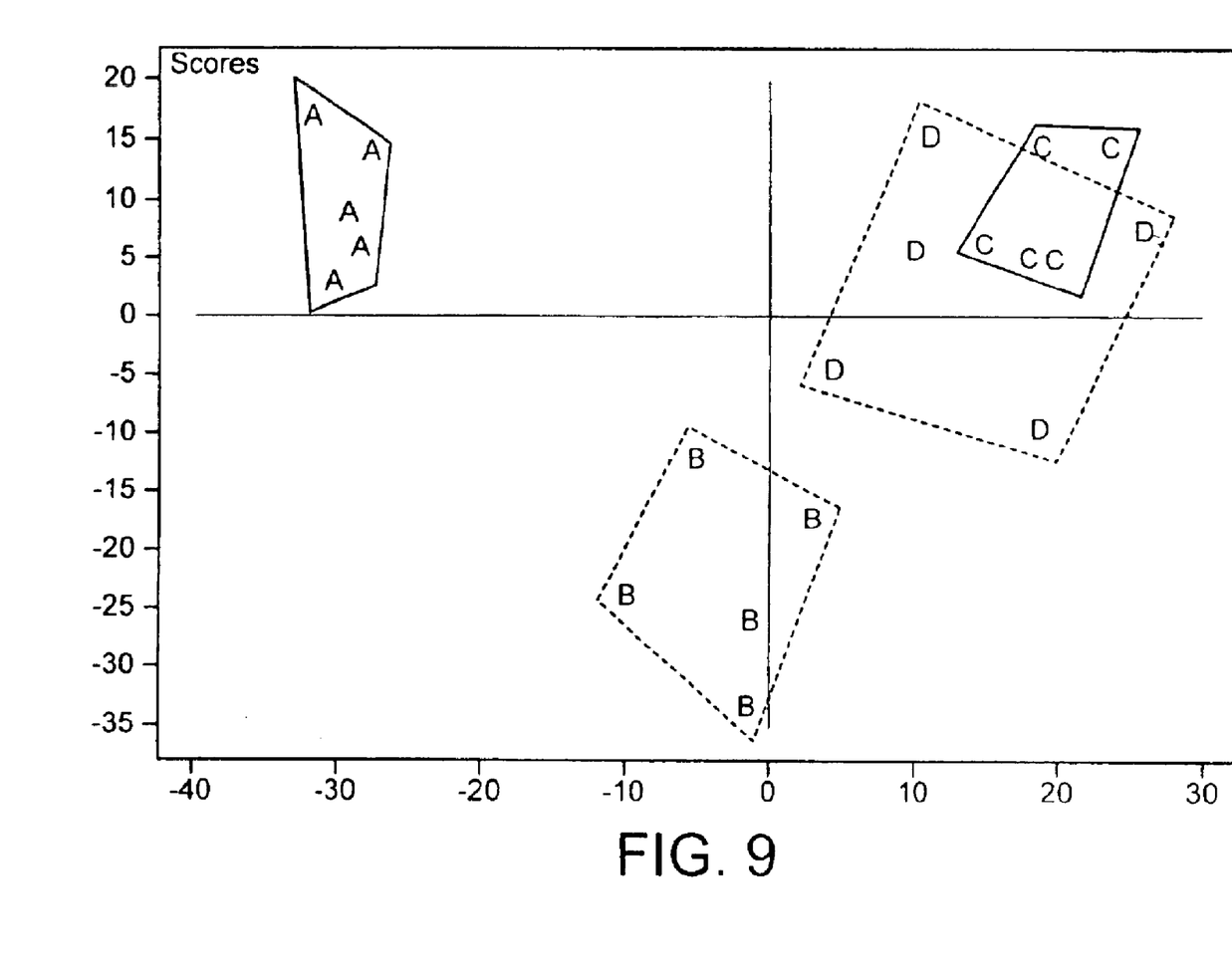
FIG. 9 shows a score plot (t1t2) of five replicates of each of the polymers designated A, B, C and D.

Data were pretreated as shown in FIG. 2 example 1. FIG. 9 shows a score plot of results: for each resin five replicates were run.

The data show the method to be able to separate between individual lots from a commercial polymerisation.

What is claimed is:

1. A method of characterising a polymer under test, comprising:

flowing said polymer through a conduit in a controlled manner such that said polymer experiences a predetermined flow rate, detecting acoustic emissions from said polymer flowing in the conduit to provide acoustic emission data relating solely to said polymer, and comparing the acoustic emissions data obtained against acoustic emission data from a polymer, or a series of polymers, of known characteristics, and thereby characterising the polymer.

2. A method as claimed in claim 1 wherein a rheological property of the polymer under test is thereby determined.

3. A method as claimed in claim 1 wherein the identity of the polymer under test is thereby determined.

4. A method as claimed in claim 2 wherein the rheological property under test is the viscosity of the polymer.

5. A method as claimed in claim 1 wherein the acoustic emissions are detected by means of an accelerometer.

6. A method as claimed in claim 1 wherein said conduit is associated with a pipe leading directly from a polymerisation reactor.

7. A method as claimed in claim 1 wherein said conduit is associated with an extruder.

8. A method as claimed in claim 1 wherein said conduit comprises a structural detail altering flow characteristics of the polymer flowing in the conduit.

9. A method as claimed in claim 1 wherein the acoustic emissions data is analysed using Principal Component Analysis (PCA) techniques.

10. An apparatus for characterising a molten polymer, comprising:

a) means for controlling the flow of said polymer through a conduit such that the polymer experiences a predetermined flow rate;

b) an acoustic sensor capable of detecting acoustic emissions from the polymer and thereby generating a signal relating solely to acoustic emissions data from said polymer; and c) means for comparing the signal against acoustic emissions data from molten polymers of known characteristics.

11. An apparatus as claimed in claim 10, wherein said apparatus is adapted whereby to determine a value for a desired rheological property of the polymer under test.

12. An apparatus as claimed in claim 10, wherein said apparatus further comprises means for identifying the polymer.

* * * * *